(12) United States Patent
Bansal

(10) Patent No.: US 8,680,075 B2
(45) Date of Patent: Mar. 25, 2014

(54) METHODS AND COMPOSITIONS FOR INHIBITING CELLULAR PROLIFERATION AND SURGICAL ADHESION

(75) Inventor: Rekha Bansal, Twinsburg, OH (US)

(73) Assignee: Novelmed Therapeutics, Inc., Cleveland, OH (US)

( * ) Notice: Subject to any disclaimer, the term of this patent is extended or adjusted under 35 U.S.C. 154(b) by 0 days.

(21) Appl. No.: 13/202,006

(22) PCT Filed: Feb. 17, 2010

(86) PCT No.: PCT/US2010/024452
§ 371 (c)(1), (2), (4) Date: Aug. 17, 2011

(87) PCT Pub. No.: WO2010/096466
PCT Pub. Date: Aug. 26, 2010

(65) Prior Publication Data
US 2012/0040928 A1 Feb. 16, 2012

Related U.S. Application Data

(60) Provisional application No. 61/152,988, filed on Feb. 17, 2009.

(51) Int. Cl.
*A61K 31/737* (2006.01)
*A61K 31/721* (2006.01)
*A61K 31/715* (2006.01)
*C08B 37/02* (2006.01)

(52) U.S. Cl.
USPC ............. 514/59; 514/54; 514/56; 536/112; 536/123.1; 536/55.1

(58) Field of Classification Search
USPC ............ 514/54, 59, 56, 55.1; 536/123.1, 112, 536/55.1
See application file for complete search history.

(56) References Cited

U.S. PATENT DOCUMENTS 6,417,173 B1 * 7/2002 Roufa et al. ............. 514/54
2005/0183731 A1 * 8/2005 Hunter et al. ............ 128/898

* cited by examiner

*Primary Examiner* — Shaojia Anna Jiang
*Assistant Examiner* — Michael C Henry
(74) *Attorney, Agent, or Firm* — Tarolli, Sundheim, Covell & Tummino LLP

(57) ABSTRACT

A method for inhibiting cellular proliferation of fibroblasts and/or glioma cells in a mammal includes administering a composition to a mammal wherein the composition includes an amount of an anionic polymer and an anti-platelet agent effective to inhibit cellular proliferation of fibroblasts and gliomas in the mammal.

11 Claims, 15 Drawing Sheets

Figs. 11A-B

METHODS AND COMPOSITIONS FOR INHIBITING CELLULAR PROLIFERATION AND SURGICAL ADHESION

RELATED APPLICATION

This application corresponds to PCT/US2010/024452, filed Feb. 17, 2010, which claims the benefit of U.S. Provisional Application No. 61/152,988, filed Feb. 17, 2009, the subject matter, which is herein incorporated by reference in its entirety.

TECHNICAL FIELD

The present invention is directed to methods and compositions of inhibiting and/or preventing cellular proliferation and adhesions that form during surgery.

BACKGROUND OF THE INVENTION

Approximately, 1.8 million abdominal surgeries are performed in United States; out of which postoperative adhesions occur in 67-93% patients who underwent abdominal surgery. Annual expense of removing abdominal adhesions cost the United States in excess of 2 billion dollars. Worldwide total surgical procedures are as follows: Lumbar (800,000), Tendon/Nerve (500,000), Abdominal (2 million), Pelvic (2.6 million, Implants (2 million), and cardiac (2 million). All these surgical procedures can cause severe adhesions. While adhesions are inevitable in several surgeries, however good surgical techniques can have better chance of success without having much adhesions. Organs or tissues attach to each other via scar tissue and introduce clinical problems. While the formation of scar tissue is part of the normal healing process and is required for proper wound healing, in some cases the scar tissue overgrows the intended region and creates adhesions. Formation of such adhesions restrict the normal mobility and function of affected body parts and are therefore named as complications of the surgery. Adhesions can be very painful and sometimes can become fatal and result in paralysis of functions of various body organs. As a result of the surgical insult, unwanted attachments occur between the organs or the tissues via scar tissue. As a consequence of the surgical adhesions, the patient can suffer from pain, functional deficit, intestinal obstruction, female infertility and prolong and complicated re-operation.

SUMMARY OF THE INVENTION

The present invention relates to compositions and methods for inhibiting and/or preventing cellular proliferation and adhesions that form during surgery. The compositions can include an anionic monomer or polymer and a compound that prevents platelet activation and/or platelet aggregation (i.e., an anti-platelet agent).

In one aspect of the invention, the anti-platelet agent can be covalently linked to the anionic monomer or polymer to form a conjugate compound. The conjugate compound can be mixed with a semisolid carrier, such as GELFOAM, to generate a device for implantation at the surgical site.

In another aspect of the invention, the anionic monomer/polymer and the anti-platelet agent can be present in a formulation without the covalent bond between the anionic polymer/monomer and the anti-platelet agent.

The present invention also relates to methods of using such compositions to inhibit invasion and proliferation resulting in fibrosis and attendant complications, such as scar formation and surgical adhesions.

The present invention demonstrates that compositions including polymers (or monomers) having a molecular weight of about 500 Daltons to about 500,000 Daltons, which are anionic in nature and have anti-platelet damaging property, in combination with anti-platelet agents, such as inhibitors of glycoprotein (GP) IIb/IIIa receptors in human platelets, can effectively inhibit scar formation, in particular surgical adhesions, and that these compositions inhibit cell invasion and peridural fibrosis. Such compositions are useful in inhibiting fibroblast invasion, thus regulating both the wound-healing process and preventing fibrosis. These compositions can inhibit cell proliferation, cell invasion, monocyte and neutrophil cell infiltration into the surgical site.

The anionic polymer or monomer can include dextran sulfate, pentosan polysulfate in addition to glycosaminoglycans, such as dermatan sulfate, chondroitin sulfate, keratan sulfate, heparan sulfate, heparin, and alginate. These molecules can inhibit fibroblast proliferation, invasion or migration. In one example, the anionic polymer used in the compositions can include dextran sulfate.

The anti-platelet agent can be a synthetic compound, protein, polypeptide, or antibody. The anti-platelet agent can include inhibitors of glycoprotein (GP) IIb/IIIa receptors in human platelets, as well as anticoagulants that inhibit platelet aggregation. In one example, the anti-platelet agent can include Tirofiban (AGGRASTAT, Merck), which is a glycoprotein (GP) IIb/IIIa inhibitor.

The present invention is further directed to methods of using an inhibitory anionic conjugate, preferably with the dextran sulfate moiety combined with Tirofiban to inhibit fibroblast invasion and fibrosis, and promote wound healing as a result of platelet preservation. The invention therefore provides methods to inhibit fibroblast invasion, glial invasion, and promote wound healing. In one embodiment, the anti-platelet agent can be attached to the dextran sulfate molecule to provide both inhibition of scar formation and promotion of wound healing.

The instant invention further provides compositions comprising inhibitory anionic compound conjugate and an anti-platelet agent and methods to administer the compositions to inhibit scar formation via the inhibition of invasion of glial cells. The present invention also provides compositions comprising effective amounts of an inhibitory conjugate compound comprising, for example, dextran sulfate-Tirofiban conjugate and an effective amount of an adhesive protein, and a pharmaceutically acceptable carrier.

DETAILED DESCRIPTION

Figure 1:
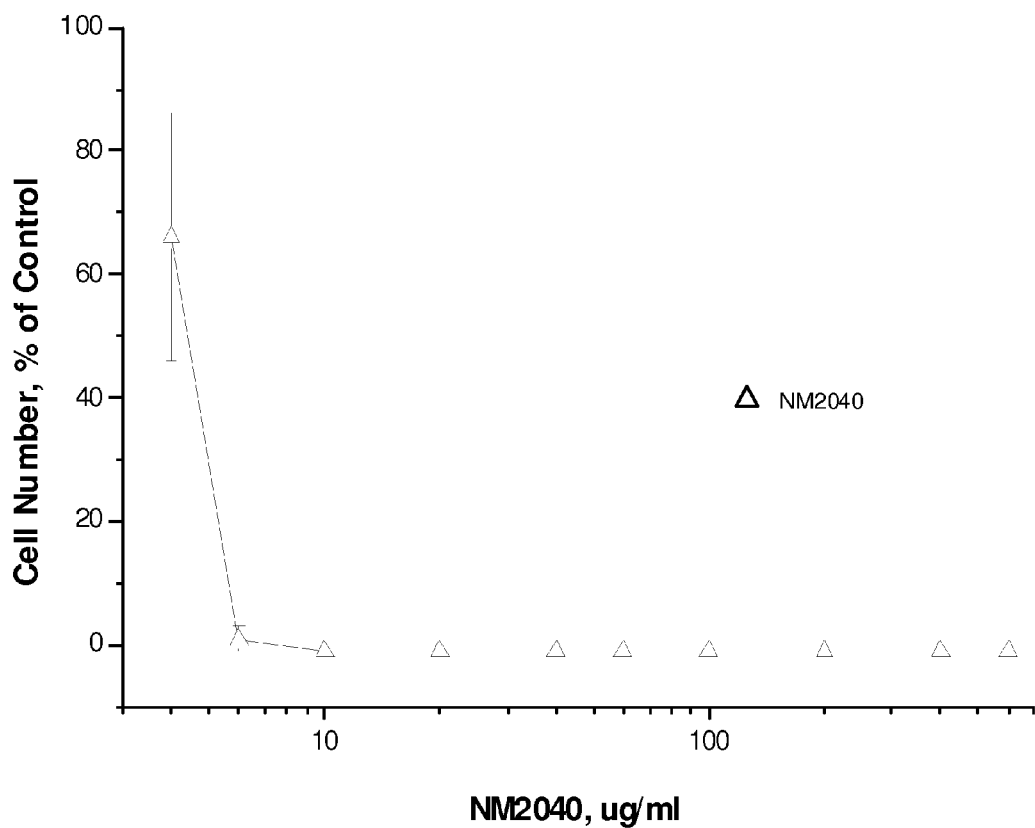
FIG. 1 illustrates NM2040 Inhibits 3T3 Cell Proliferation.

The present invention relates to pharmaceutical compositions that can effectively inhibit scar formation and, in particular, surgical adhesions. The composition includes anionic compounds, such as an anionic polymer (or monomer) that can be mixed with or conjugated with a compound that prevents platelet activation and/or platelet aggregation (i.e., an anti-platelet agent). Such compositions can prevent fibrosis and infiltration of neutrophils and monocytes at the site. The compositions can effectively inhibit invasion of cells associated with detrimental healing processes, e.g., fibrosis and scarring. The compositions of the present invention are also useful in inhibiting fibroblast invasion, thus regulating the healing process and preventing fibrosis. The compositions of the present invention can also inhibit glial-cell invasion, neutrophil and monocyte/macrophage invasion. In one example, a composition comprising an anionic polymer in combination with the anti-platelet agent Tirofiban can inhibit glial cell invasion, 3T3 cell invasion, neutrophil and monocyte invasion. Thus, the present invention teaches a large number of materials for use in inhibition of scar formation, fibrosis, and surgical adhesions.

The anionic compound used in the composition of the present invention can include anionic polymers (and/or monomers), such as dextran sulfate (DX) and pentosan polysulfate (PS), dermatan sulfate (DS), chondroitin sulfate (CS), keratan sulfate (KS), heparan sulfate (HS), Fragmin, and heparin (HN). At suitable concentrations, the foregoing molecules can inhibit fibroblast invasion or migration.

In one embodiment, the present invention is directed to methods of using DX, and molecules and compositions comprising DX, to inhibit, prevent or regulate fibroblast invasion and fibrosis and therapeutically, where the foregoing is desired. The Dextran Sulfate in accordance with the present invention can have a molecular weight of greater than about 500 Daltons and a sulfur content of greater than about 2%, by weight. In one example, the Dextran Sulfate can have a molecular weight of about 500 Daltons to about 500,000 Daltons and a sulfate content of about 12% to about 18%, by weight.

In one example, the anti-platelet agent can include ticlopidine and/or clopidogrel. Ticlopidine (marketed as Ticlid by Roche US Pharmaceuticals) has a proposed mechanism of action that interferes selectively with ADP-induced transformation of GPIIb/IIIa complex expression in activated platelets. Ticlopidine is used especially in patients where aspirin is not tolerated. It also inhibits platelet aggregation induced by thrombin, collagen, arachidonic acid, and platelet-activating factor. Ticlopidine administered in a dose of 250 mg, twice daily, reduced the incidence of a combined endpoint of stroke, myocardial infarction, or vascular death by roughly 30%. Due to the increased risk of thrombotic thrombocytopenic pupura (TTP) and neutropenia, Ticlopidine was replaced by the newer drug Clopidogrel. Clopidogrel (marketed as Plavix-Bristol Myers) is another ADP antagonist that inhibits the binding of fibrinogen to its platelet receptor, the GPIIb/IIIa integrin. It does not directly modify the GPIIb/IIIa complex, suggesting that Clopidogrel acts indirectly to reduce fibrinogen binding.

In yet another example, the anti-platelet agent can include a GPIIb/IIIa inhibitor. Glycoprotein IIb/IIIa receptor is expressed following agonist stimulation. This receptor binds with multiple adhesive ligand molecules, including fibrinogen, vWF (in conditions of high shear as might exist in stenotic arteries), fibronectin, vitronectin, and thrombospondin, which causes platelets to aggregate. Platelet recruitment is inhibited by anti-GPIIb/IIIa agents, such as monoclonal antibodies (c7E—ReoPro), cyclic peptide sequences (Eptifibatide-Integrilin), and by synthetic competitive analogues (Tirofiban—AGGRASTAT) Calvete, J. J., Platelet integrin GPIIb/IIIa: structure-function correlations. An update and lessons from other integrins. Proceedings of the Society for Experimental Biology and Medicine, 1999. 222(1): p. 29; Gabriel, H. M. and E. I. Oliveira, Role of abciximab in the treatment of coronary artery disease. Expert Opinion on Biological Therapy, 2006. 6(9): p. 935; Lal, H., et al., Integrins: novel therapeutic targets for cardiovascular diseases. Cardiovascular & Hematological Agents in Medicinal Chemistry, 2007. 5(2): p. 109; Menozzi, A., P. A. Merlini, and D. Ardissino, Tirofiban in acute coronary syndromes. Expert Review of Cardiovascular Therapy, 2005. 3(2): p. 193; Ringleb, P. A., Thrombolytics, anticoagulants, and antiplatelet agents. Stroke, 2006. 37(2): p. 312). The monoclonal antibody c7E3 (Abciximab or ReoPro produced by Centocor) inhibits the GPIIb/IIIa receptor, has undergone extensive clinical trials and received approval for clinical use. It has been shown to prevent thrombus formation after vascular injury and to be effective in reducing early reocclusion following coronary interventional procedures (Expert Opinion on Biological Therapy, 2006. 6(9): p. 935) Abciximab is a popular drug at BUMC and ranks in the top in annual pharmaceutical expenditures (The Baylor Drug Newsletter, June 1998; 10 (Crit. Rev Immunol, 1981. 1(4): p. 321-66)). The plasma half-life of Abciximab is short in plasma but the antibody can bind to the GPIIb/IIIa receptor for long periods of time after termination of treatment.

Nonpeptide antagonists that mimic the charge and geometric characteristics of the arginine-glycine-aspartic acid sequence have been developed. These agents have the potential to be orally administered and, thus, effective for chronic antiplatelet therapy. Tirofiban (marketed as AGGRASTAT by MERCK), received new drug approval in May 1998 for clinical use.

Naturally occurring GPIIb/IIIa-antagonist peptides have been discovered and characterized in vitro and in vivo as Eptifibatide (Integrilin—Millennium Pharmaceuticals).

Eptifibatide is a cyclic heptapeptide with a lysine-glycine-aspartic acid sequence rather than an arginine-glycine-aspartic acid sequence.

In one embodiment of the invention, the composition can comprise a conjugate of an anionic polymer and an anti-platelet agent that are conjugated by covalent bonding. For example, the conjugate can comprise dextran sulfate conjugated to Tirofiban. The conjugate can be administered to a subject at a desired site at an amount effective to inhibit scar formations and surgical adhesions.

In another embodiment, the conjugate can comprise a mixture of an anionic polymer and an anti-platelet agent. For example, the conjugate can comprise a mixture of dextran sulfate and Tirofiban. The mixture can be administered to a subject at a desired site at an amount effective to inhibit scar formations and surgical adhesions.

The instant invention further provides pharmaceutical compositions comprising an anionic polymer or monomer and an anti-platelet agent in a pharmaceutically acceptable carrier, and—methods to administer the compositions to inhibit scar formation, and fibrosis to inhibit undesired invasion of glial cells, fibroblasts, and neurite outgrowth.

The compositions and methods of the present invention are suitable for treatment of animals, preferably mammals, and more preferably humans. A therapeutically effective amount of a composition comprising a conjugate compound of the invention can be administered to a lesion in an animal for any of the methods disclosed.

Compositions to Prevent Fibrosis and Cell Invasion

The invention provides compositions for use in inhibiting fibroblast invasion, glial cell invasion, neurite outgrowth, neutrophil invasion, neutrophil and monocyte/macrophage invasion. In particular, the compositions are useful in preventing fibrosis and scar formation, e.g., surgical adhesions. The anionic polymers used in the compositions should preferably be present at a concentration greater than about 1 mg/ml, more preferably in the range of 20-200 mg/ml. In one example, the anionic polymer is dextran sulfate and the anti-platelet agent is Tirofiban. In one particular example, the dextran sulfate can have a sulfur content of at least about 10% by weight.

The composition comprising the anionic polymer and the anti-platelet agent can be mixed with a carrier or excipient, such as saline and gelfoam to form a viscous liquid or gel. It will be appreciated that the anionic polymer and the anti-platelet agent may be combined with a solid or semi-solid excipient or carrier, such as paste, gel, foam or sheet. The anionic polymer and the anti-platelet agent may be mixed with the carrier or excipient in a colloidal suspension or admixture; alternatively, the carrier or excipient may be impregnated with the conjugate compound to form the composition. Preferred semi-solid carriers include dextran gels, such as HYSKON-70 (Pharmacia), INTERCEED (Johnson & Johnson), native collagen gels, and denatured collagen gels, such as GELFOAM (Upjohn).

General Indications: The compositions of the present invention can be used as barriers to cell migration or invasion caused by trauma, surgery, infection (viral or bacterial), metabolic disease, malignancy, exposure to toxic agents, and other hyperplastic situations. Coating an organ or tissue with the compositions may be preventive or prophylactic. Inhibitory-adhesive compositions provide a preferred coating composition.

Surgery: In one embodiment, epidural (or peridural) fibrosis may be inhibited by application of a composition of the instant invention to the surgical lesion. The compositions can be in solution, bound to substrate, trapped in a carrier protein or polymer. In one embodiment, the conjugate compound may be applied in a carrier or excipient such as a paste, gel, or sheet.

In yet another embodiment, the present invention provides a composition and method to inhibit fibrosis and scarring of fallopian tissue. In particular, fibrosis and scarring of lesions in and around the fallopian tube subsequent to surgery can be inhibited. Fibrosis of fallopian tubes, resulting from infection or other causes, is a cause of infertility in 25-30% of the cases. Pelvic sidewall adhesions are also implicated in infertility. Since scar tissue forms subsequent to surgery, surgical removal of adhesions alone is not adequate treatment. Thus, the present invention has an important application in management of infertility. Other surgical indications include but are not limited to abdominal surgery, joint surgery, tendon surgery, surgery to remove pelvic sidewall adhesions, peritoneal surgery, thoracic surgery, vascular surgery, and cardiac surgery, in particular bypass surgery, valve replacement surgery, cardiovascular surgery, or other open heart surgery.

In another embodiment, the compositions of the invention may be used in a method of inhibiting fibrosis around an implant comprising applying a composition containing therapeutically effective amount of the anionic polymer and the anti-platelet agent. Examples of implants where inhibition of scar formation and fibrosis is desired include, but are not limited to, nephrostomy tube, peritoneal drainage tube, artificial hip joint, artificial heart valve, peripheral nerve repair and other prostheses and intravenous catheter. Implants may be treated by coating or impregnating with a composition provided by the invention.

Treatment of Fibrotic Lesions in Joints: Joint lesions are corrected using surgical procedures, which can cause adhesions. These processes have the disadvantage of inducing further fibrosis during the healing process. Administration of a composition comprising anionic polymer and the anti-platelet agent of the present invention would inhibit subsequent fibrosis and adhesion formation in the joint, thus increasing the chance of successful therapy.

Modes of Administration: The compositions of the present invention can be mixed with the collagen gels using methods well known in the art to make an implantable device for prevention of adhesion that form following surgery. Such compositions of the invention will be placed into and around the site of interest by any suitable route. This may be achieved by, for example, but not by way of limitation, local infusion or application during surgery, by injection, by aerosol, by means of a catheter, or by means of an implant, said implant being of porous, non-porous, or gelatinous material, including membranes, such as silastic membranes, or fibers. In a preferred embodiment, the implant is coated or impregnated with the composition of this invention. Polymer implants treated with the composition, can be applied or inserted at the desired site of treatment. Such polymers can have various compositions, pore sizes, and geometries. Polymers that can be used include but are not limited to those made of nitrocellulose, polyanhydrides, and acrylic polymers.

The invention provides for application of a composition comprising the anionic polymer and the anti-platelet agent by surgical procedures. The composition may be applied—to a surgical wound. The composition may be directly applied to sites of tissue injury, to coat an entire organ, or to close a surgical incision. Where suitable, administration of the composition may be made by orthroscopic procedures.

EXAMPLES

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example-1

NM2040 Inhibits 3T3 Proliferation

Approximately 50,000 cells were plated in a 96 well ELISA plate. The cells were allowed to grow in DMEM with 10% FCS media for 5 days, following which the cells were treated with Cy Quant assay and the inhibition of cellular proliferation was measured using the decreased fluorescence intensity. To evaluate the effect of various concentrations of NM2040 in the cellular proliferation assay, cultures were treated with concentrations ranging from 1 to 600 µg/ml. The total fluorescence intensity was plotted against the concentrations.

Example-2

NM2040 Inhibits Glioma Proliferation

Figure 2:
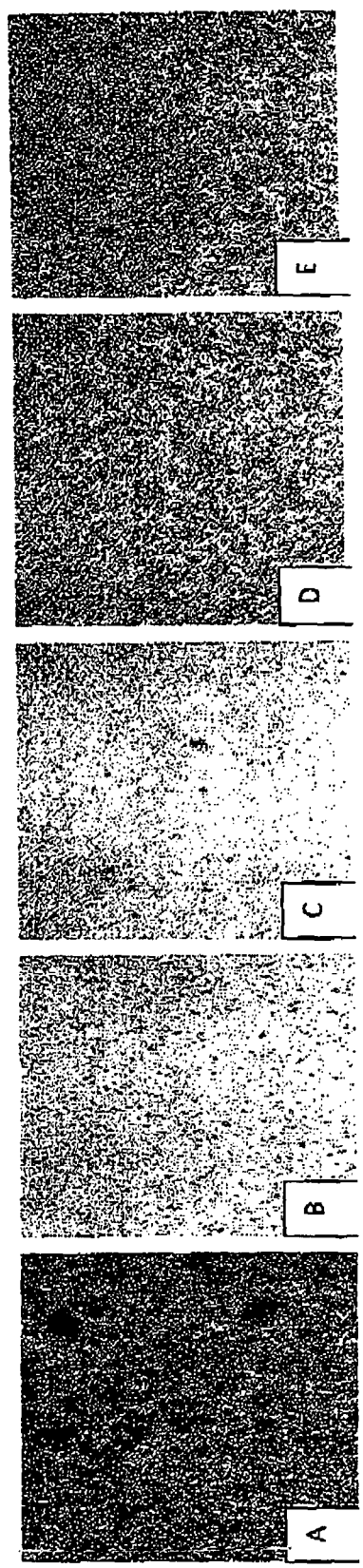
FIG. 2 illustrates NM2040 Inhibits Glioma Proliferation.

This experiment was conducted to demonstrate if NM2040 would inhibit cellular proliferation. In a six well plate, a cloning ring of 6 mm diameter was placed and 60 µl aliquot of cellular suspension (stock containing 320,000 cells/ml of C6 cells) was prepared and placed in the center of each well of a six well plate in the cloning ring. After 4 h, the media was removed and the cells were incubated with Opti-MEM 1× media with and without the compound. These cultures were incubated at 37° C. and with 10% $CO_2$ for five days, following which the pictures were taken as shown in FIG. 2. The compound effect appears to be dose dependent with maximal effect shown at 3 µg/ml. The first panel is for controls (untreated), the second panel at 3 mg/ml, the third panel at 1.5 mg/ml, the fourth panel at 0.75 mg/ml, and the fifth panel at 0.36 mg/ml. The compound NM2040 appears to be inhibitory at all doses with maximal effect seen at nearly 1 mg/ml concentration.

Example-3

Inhibition of C3a and C5a Formation by NM2040

Figure 3:
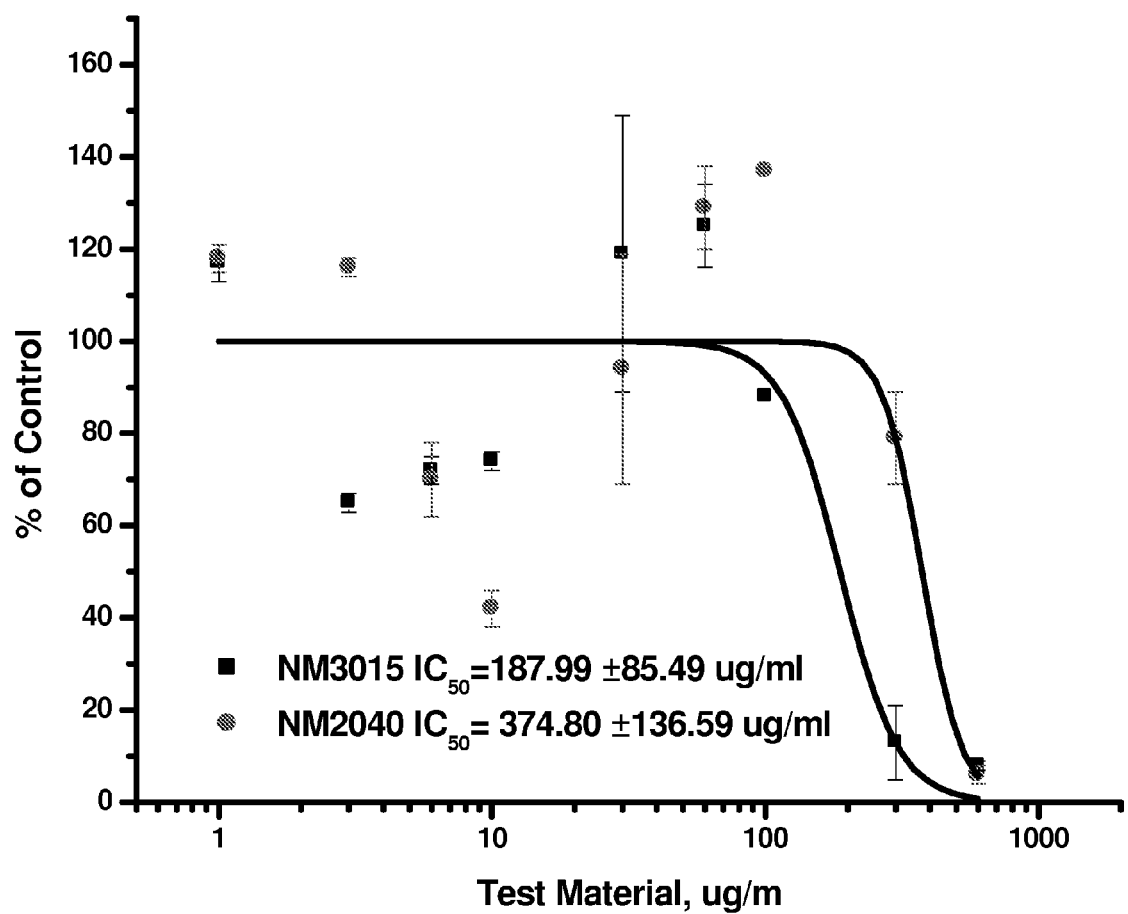
FIG. 3 illustrates NM2040 Inhibits C3a and C5a Formation.
Figure 4:
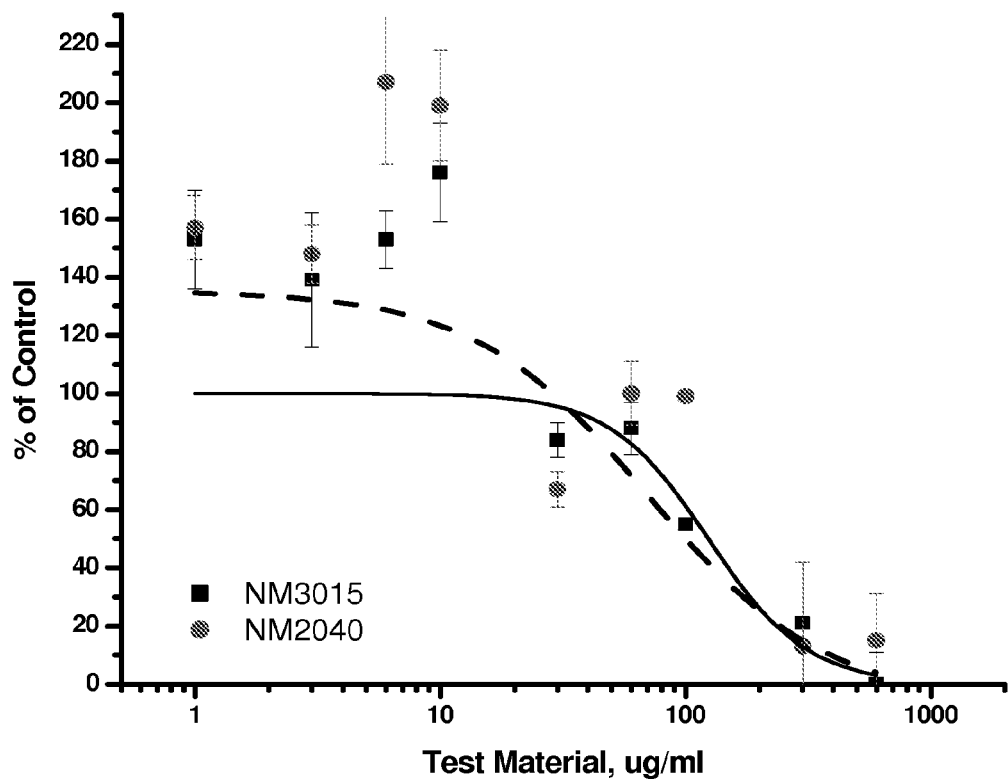
FIG. 4 illustrates NM2040 Inhibits C3a and C5a Formation.
Figure 5:
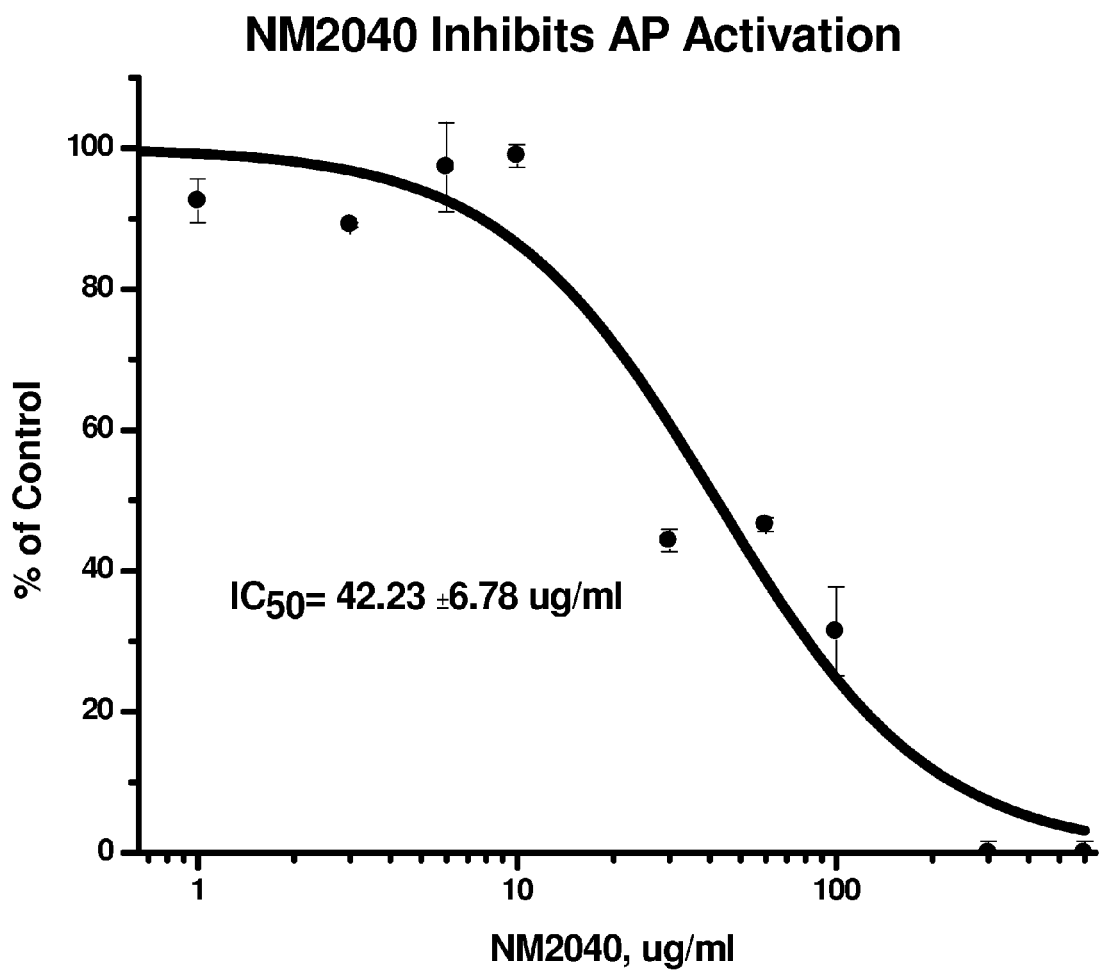
FIG. 5 illustrates NM2040 Inhibits AP activation.

Chemotactic peptides are produced at the injury site, which can attract inflammatory cells at the injury site causing inflammation. NM2040 was tested to determine if this compound would inhibit the production of the C3a and C5a. The compound was incubated with blood at 37 degree in a rotating tubing loops. Whole blood from a healthy donor was collected into a polypropylene tube containing 5 units of heparin per ml of whole blood. The whole blood was diluted 1:1 with plasmalyte and aliquoted in 2 ml aliquots with and without drug treatments. PVC tubings of 4 mm diameter were filled with 2.0 ml of the heparinized human blood and closed into a loop with a short piece of silicon tubing. Sample and control tubing loops were rotated vertically in a water bath for 2 hours at 37° C. After incubation, blood samples were transferred into 5 ml siliconized eppendorf tubes. The samples were separated into two aliquots; one aliquot was subjected to flow cytometry studies and the other aliquot was centrifuged to separate the plasma for the measurement of C3a and C5a. The plasma samples were diluted to 5% with sample diluent buffer and the amounts of C3a and C5a were determined using ELISA assay kits following the manufacturer's instructions (Quidel Corporation, San Diego Calif.). As shown in FIG. 3, and FIG. 4 NM2040 is able to prevent C3a and C5a production in a dose dependent manner. Both C3a and C5a are chemotactic peptides that are responsible for chemotaxis of neutrophils and monocytes. As shown in FIG. 5, NM2040 inhibits activation of the alternative pathway. In the same experiment, NM3015 was also evaluated. This compound is a mixture of Dextran sulfate and Tirofiban.

Example-4

Inhibition of Platelet Damage by NM2040

Figure 6:
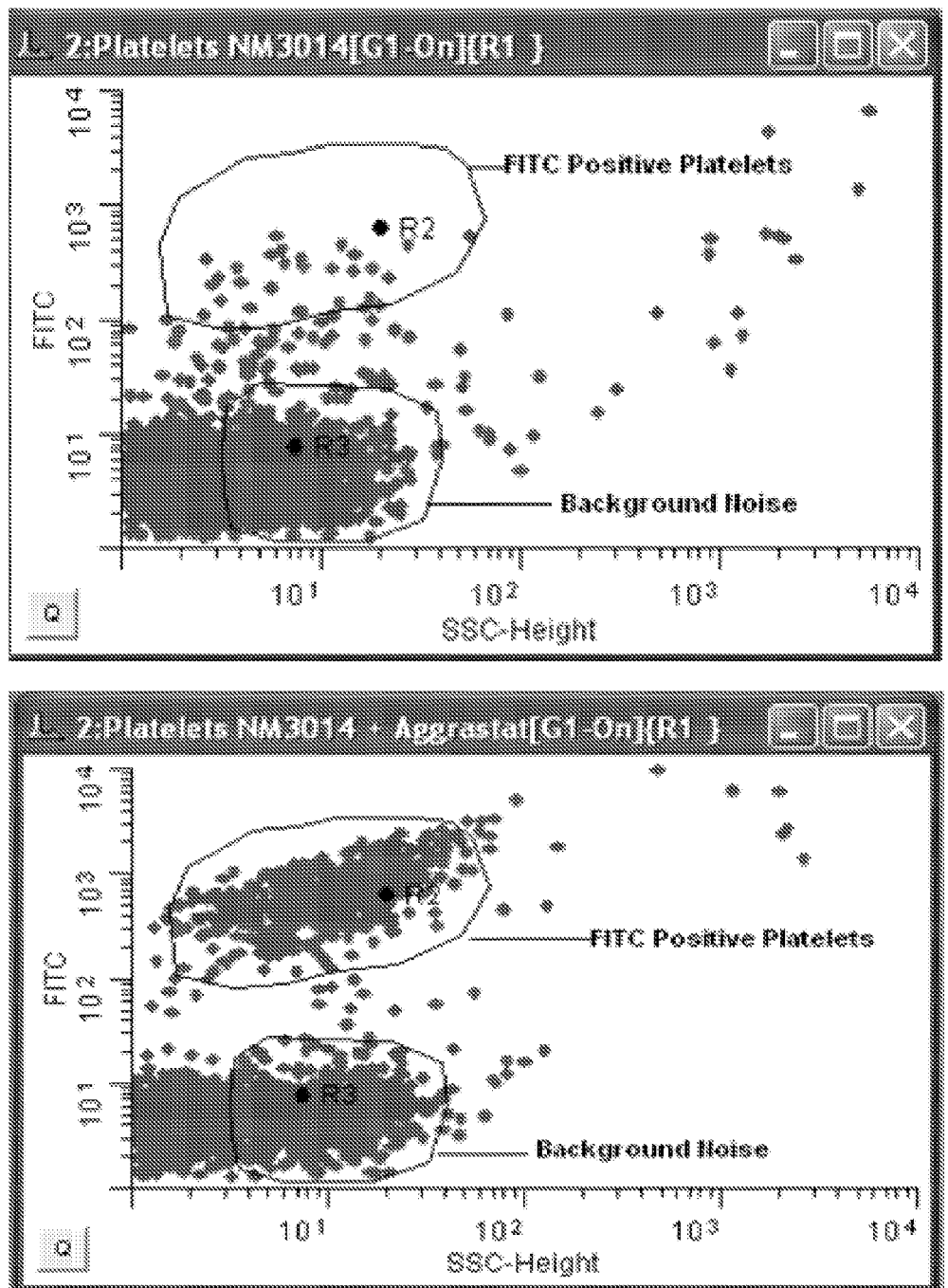
FIG. 6 illustrates NM2040 Inhibits does not affect Platelet Number.
Figure 7:
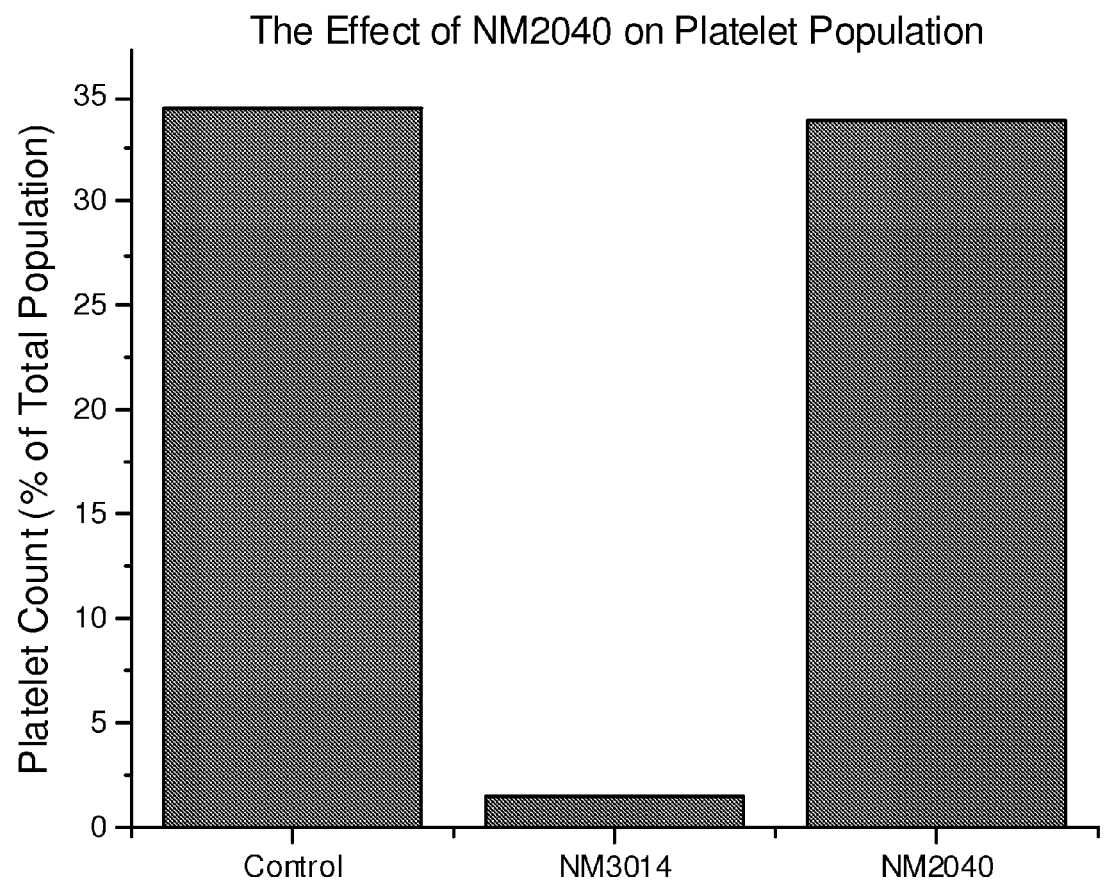
FIG. 7 illustrates inhibition of Platelet Damage by NM2040.

Aliquots of blood following the tubing loop were stained with fluorescent labeled antibodies for flow cytometry studies. Platelets were stained with FITC labeled CD61 and PE labeled CD62P. In a typical method, 20 µl of each of the labeled antibodies were added to the 100 µl of staining buffer containing 50 µl of whole blood. After 20 minutes, 2.0 ml of staining solution was added and the red blood cells were allowed to lyse for 20 minutes. The solution was centrifuged and the cell pellet was washed with PBS and suspended in 0.5 ml of para-formaldehyde solution. The samples were subjected to flow cytometry using CellQuest, BD-LSR I and the data were analyzed using WinList 5.0. Ln Median was used for calculating the shift in CD11b staining for neutrophils and monocytes. Total number of platelets were examined. As shown in FIG. 6 (lower panel) & FIG. 7, NM2040 does not affect the platelets. FITC positive platelets are those platelets that are not damaged and fall in the zone of normal platelets. In contrary, NM3014, which is Dextran Sulfate with a molecular weight of 40,000 Daltons and has an 18-20% by weight sulfate content, causes greater than 95% loss of total platelets (top panel).

Example-5

Inhibition of Neutrophil, Monocyte and Platelet Activation by NM2040

Figure 8:
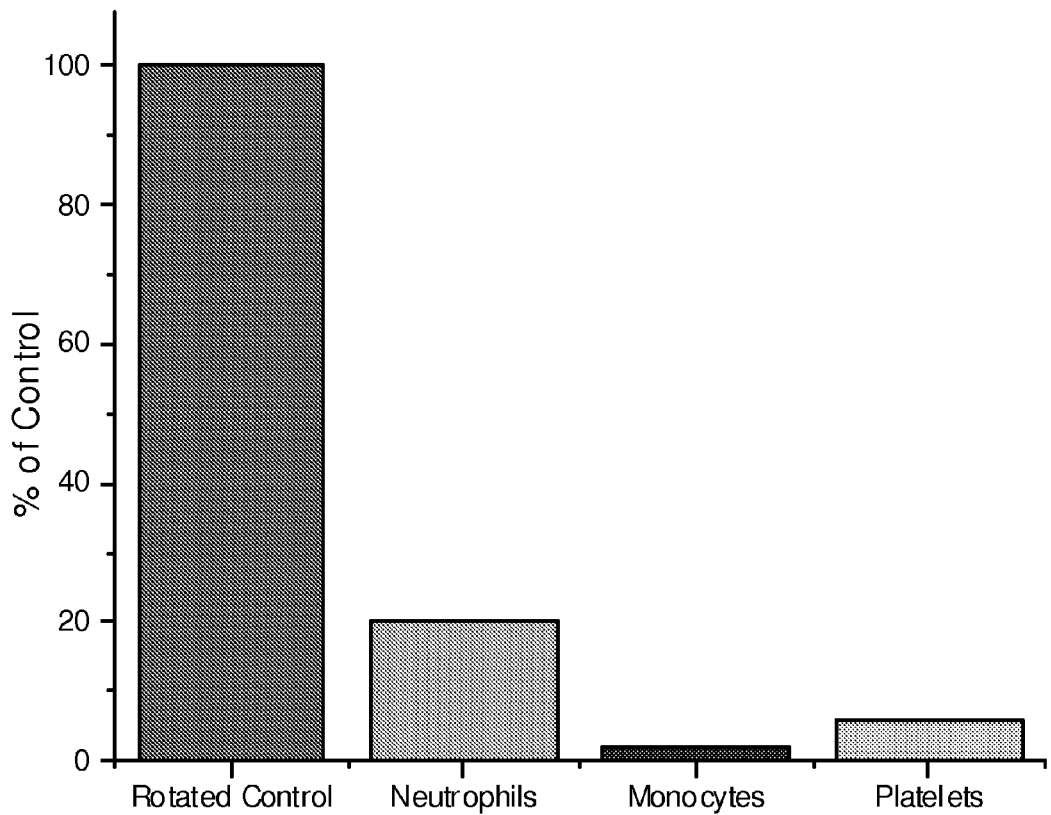
FIG. 8 illustrates NM2040 Inhibits Neutrophil, Monocyte and Platelet Activation.

Aliquots of blood following the tubing loop were stained with fluorescent labeled antibodies for flow cytometry studies. For Example; neutrophils were labeled with FITC labeled CD15 and PE labeled CD11b antibodies, monocytes were stained with FITC labeled CD14 and PE labeled CD11b antibodies, and platelets were stained with FITC labeled CD61 and PE labeled CD62P. In a typical method, 20 µl of each of the labeled antibodies were added to the 100 µl of staining buffer containing 50 µl of whole blood. After 20 minutes, 2.0 ml of staining solution was added and the red blood cells were allowed to lyse for 20 minutes. The solution was centrifuged and the cell pellet was washed with PBS and suspended in 0.5 ml of para-formaldehyde solution. The samples were subjected to flow cytometry using CellQuest, BD-LSR I and the data were analyzed using WinList 5.0. Ln Median was used for calculating the shift in CD11b staining for neutrophils and monocytes. % gated dual labeled cells were quantified for platelet populations. As shown in FIG. 8, all three cell types demonstrated significant inhibition of cellular activation.

Example-6

NM2040 Inhibits Adhesions of Spinal Cord to Surrounding Tissue (Epidural Fibrosis) in a Rat Laminectomy The scar tissue attachment to the spinal cord is believed to be the cause of long-term, recurrent pain following laminectomy procedures. The epidural fibrosis refers to the scar tissue that forms following a laminectomy procedure. Laminectomy refers to back surgery of the lamina. Scar tissue forms within the laminectomy site and binds the undersurface of the erector spinae muscles to the posterior and lateral surfaces of the dura mater and to the nerve roots exiting through the dura matter. Epidural fibrosis was investigated after lumbar laminectomy in rats. In this model, a laminectomy is performed at the lumbar 3 (L3) and 5 (L5) vertebrae and then the test agent is applied to the laminectomy site. Subsequently, the laminectomy sites are examined for fibrosis by gross dissection.

Figure 9:
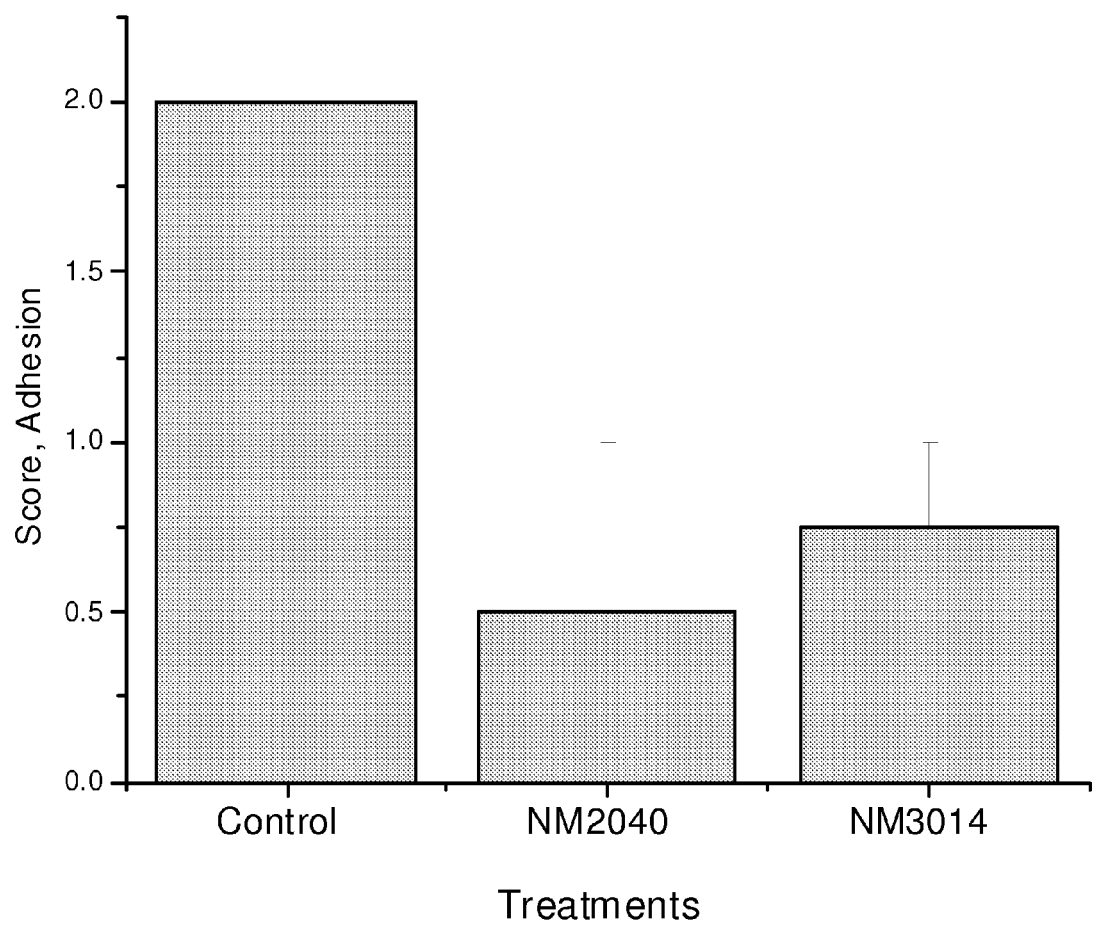
FIG. 9 illustrates NM2040 Inhibits Surgical Adhesions Following Rat Laminectomy Surgery.

Laminectomies were performed at lumbar vertebrae L3 and L5 to provide auto-controls within each animal. Gelfoam-NM2040 mix was prepared and used on Laminectomy sites in rats. Lewis inbred rats were anesthetized isofluorane. The dorsal skin was incised and the paraspinal muscles were separated from the spinous processes of lumbar vertebrae L2 through L6 to expose the L3 and L5. The spinous processes of L3 and L5 were removed and the vertebral lamina was also removed creating a rectangular laminectomy defect. The test material was placed onto the laminectomy site. The overlying paraspinal muscles were closed over the site by suturing the superficial fascia together and the skin incision was closed with wound clips. After two weeks, animals were subjected to gross evaluation. Rats were anesthetized with anestheticized with isofluorane and the surgical site was reopened by incising the skin and separating the paraspinal muscles. The site and the tissue were scored 0 to 2. 0 being the "no adhesions", 1 being the lose adhesions, and 2 being the tenacious adhesions. Following the evaluations, rats were euthanized by anesthetic overdose. In all animals, the skin incision and the underlying fascia and paraspinal muscles had healed well. At all laminectomy sites, separation of the paraspinal muscles revealed a layer of scar tissue. Sites treated with the test material demonstrated poor or no adhesion at all and majority of the scores in the group were either zero or 0.5 out of a total of two. The laminectomy site itself had not changed appreciably in size; the borders of the site appeared smooth. The saline treated site served as a negative control. As the scar tissue was removed, bleeding began in and around the site and the site had decreased in size due to adhesion tissue formation. Implantation of NM2040 into the laminectomy site resulted in scores that were significantly lower than implantation of saline controls. These results demonstrate that NM2040 is a potent agent for reducing epidural fibrosis in the rat laminectomy model. The formulation of NM2040 consisted of 10% gelfoan powder, 20 mg/ml final NM2040 in saline. The rat epidural fibrosis model clearly shows that the presence of NM2040 provides a substantial therapeutic benefit by inhibiting fibrosis. As shown in FIG. 9, NM2040 inhibits surgical adhesions in rat Laminectomy model.

Example-7

Synthesis of NM2040

Figure 10:
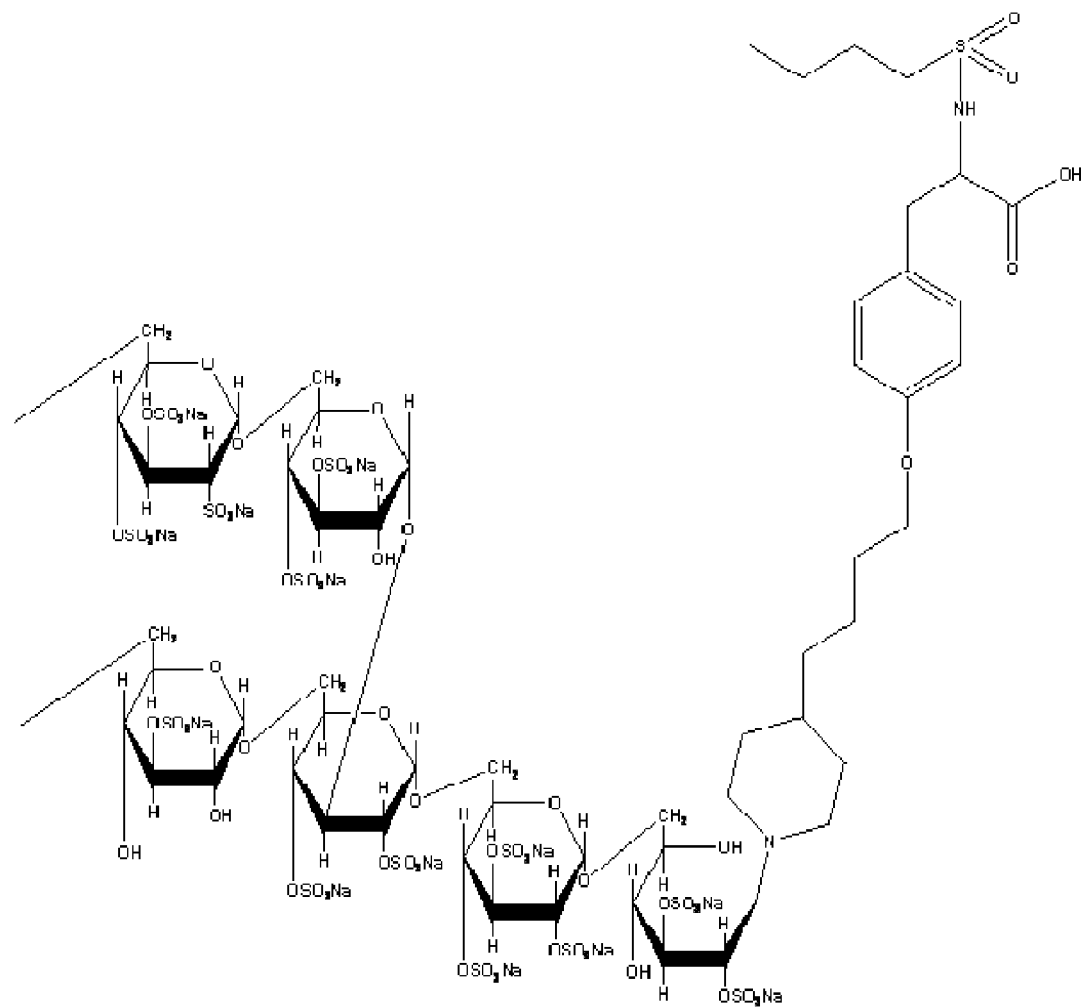
FIG. 10 illustrates NM2040 Synthesis and Structure.

Dextran sulfate has been used for prevention of surgical adhesions. This material activates platelets. As shown in FIG. 10, dextran sulfate can be conjugated to Tirofiban, which has the platelet preserving function. This conjugate compound is prepared as follows. In a 25 mL 2-neck round bottom glass flask, add 1.0 g of dextran sulfate, 2.0 mL water and 10 μL of glacial acetic acid. The contents were stirred overnight at room temperature. The final mixture appeared to be a clear solution. In a separate 10 mL 1-neck flask, add 13 mg of Tirofiban, 1 mL of methanol:water (1:1) mixture, and 10 μL of DMSO. The contents were mixed at room temperature. The final mixture appeared to be a clear solution. Solution from step 2 was added to solution from step 1 and stirred for 2.5-h. Add 315 mg of sodium cyanoborohydride in parts over a period of 15 mins and allow the reaction to proceed for 48 h while monitoring on HPLC. The final solution appeared to be clear. The purification of conjugate was achieved by first filtering through a membrane filter and then through a size-exclusion column. At the end of 48 h, the solution mixture was transferred onto a filter (MWCO 3000, MICRON YM-3) in 500 μL batches and centrifuged at 4000 rpm (1431 gs/RCF) to reduce the total volume to 250 uL. Molecules with smaller molecular size like the sodium cyanoborohydride and excess Tirofiban would pass through the filter, whereas the conjugated product of dextran sulfate-Tirofiban would remain unfiltered. Fresh 250 μL of high purity water was added and the centrifugation procedure repeated to remove small molecular weight contaminants. The process was repeated 4 more times to ensure complete absence of contaminants. The final volume of 250 μL was transferred to eppendorf tubes, frozen at −80° C. and lyophilized for 24 h to get a white solid material. The sample was weighted and re-dissolved in minimum amount of high purity water for further purification using size-exclusion column chromatography. A slurry of Sephadex G-10 in water was poured into a glass column (2.5×75 cm) with the packing height of 36 cm. High purity water was used as the mobile phase at the flow rate of 0.5 mL/min Void volume of the column was ~720 mL. Fractions of 5 mL were collected every 10 mins using an automated fraction collector (Foxy 200). Each fraction was monitored using UV-VIS spectrophotometer. Fractions 4-9 were pooled based on the similarity of UV profile for Tirofiban. The 30 mL pooled volume was then transferred to a plastic tube, frozen at −80° C. and lyophilized to yield a white powder.

The molar proportions of constituents in the conjugate were obtained using the UV-Vis spectrophotometry. A standard curve was generated for pure Tirofiban. Various concentrations of Tirofiban solution in water were read at $\lambda_{max}$ 275 nm in a UV-Vis spectrophotometer. The following table shows the absorbance readings. Then the absorbance of the conjugate was measured. For a solution of 8.333 mg/mL conjugate concentration, the $A_{275}$ was found to be 0.34 AU. This corresponds to a molar proportion of 1:1.2 for dextran sulfate-Tirofiban conjugate. Both Tirofiban and dextran sulfate-Tirofiban conjugate were subjected to a reverse phase C18 HPLC column to determine if the presence of dextran sulfate in the conjugate would cause a shift in the peak position of Tirofiban. Tirofiban was monitored at 280 nm filters in C18-HPLC. Because dextran sulfate by itself does not carry any aromatic groups, it does not show much absorption at 280 nm. A 20 μL aliquot of the Tirofiban and the conjugate was injected into the column A methanol:water (1:1) mixture with a flow rate of 0.75 mL/min was used as an eluent. The dextran sulfate-Tirofiban conjugate and the unconjugated Tirofiban profiles were as shown in the figure. The conjugate elutes earlier than unconjugated Tirofiban because of its significantly higher polarity. The sample was prepared by dissolving the conjugate in 0.5 mL deuterated water ($D_2O$). NMR was recorded on INOVA-400 MHz instrument at ambient temperature. The isolated yield of the final conjugate was >95%. This conjugate has the following structure based on its NMR data. The NMR shows the presence of dextran sulfate peaks in the region 3.5-5.5 ppm corresponding to the saccharide protons, while aromatic protons of Tirofiban are seen at 7.0 and 7.2 ppm. The alkyl protons of Tirofiban are seen between 1 and 2 ppm. The chemical name of dextran sulfate-Tirofiban conjugate can be written as the conjugate of dextran sulfate and 2-(butane-1-sulfonylamino)-3-[4-(4-piperidin-4-yl-butoxy)-phenyl]-propionic acid. In this structure, the secondary amine of Tirofiban is bonded to the C-1 carbon of the saccharide monomer at the reducing end of dextran sulfate.

Example 8

NM2040 Inhibits Epidural Fibrosis after Laminectomy

Figure 11:
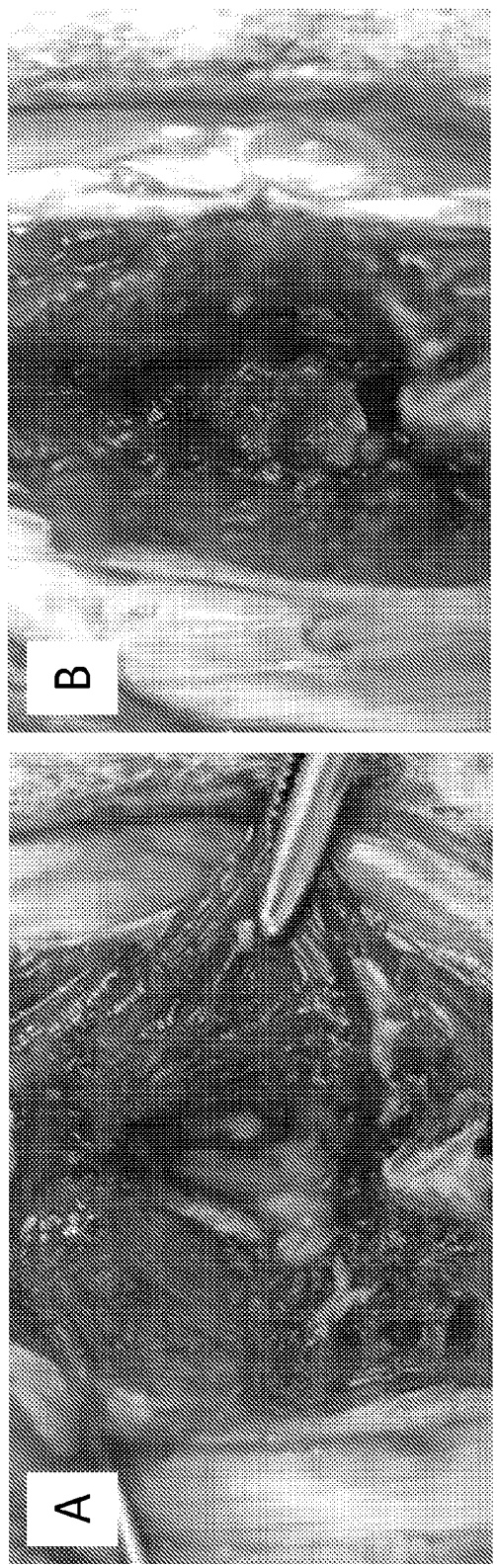
FIG. 11 illustrates rat Laminectomy site (L3) prior to placement of the test material (left panel) and showing placement of the NM2040 gel into the L3 laminectomy site (right panel).

Epidural fibrosis was investigated after laminectomies in adult Lewis rats. Laminectomies were performed at the lumbar 3 (L3) and 5 (L5) vertebrae. The test agent gel was applied to one site and saline (control) was applied to the other. Two weeks later, the laminectomy sites were examined for fibrosis by gross dissection as previously described. Briefly, rats were anesthetized. The dorsal skin was incised and the paraspinal muscles were separated from the spinous processes of lumbar vertebrae L2 through L6 to expose L3 and L5. The spinous processes of L3 and L5 and the vertebral lamina were removed, creating a rectangular laminectomy defect approximately 5×2 mm (FIG. 11A). The test material NM2040, or vehicle was placed onto the laminectomy site according to randomized, coded protocol (FIG. 11B). The formulation of NM2040 consisted of 10% gel foam powder, 20 mg/ml final concentration in sterile saline. The mixtures were placed in a syringe, autoclaved and allowed to cool to room temperature prior to placement into the laminectomy site. The fascia overlying the paraspinal muscles was sutured 5-0 polydoxanone PDS resorbable suture (Ethicon) and the skin incision was closed with 7.5 mm Michel wound clips. After two weeks, animals were anesthetized and subjected to gross evaluation. For gross evaluation, the wound site was reopened by incising the skin and separating the paraspinal muscles. Epidural scar formation was designated as the connective tissue between the test material and the dura mater. The thickness and toughness of the deep scar was evaluated by blunt dissection and scored 0 to 2.0 being the "no adhesions" with the dura mater clearly visible, 1 being a thin, lose connective tissue covering the dura that was easily removed, and 2 being a thick, dense tenacious adhesion that was difficult to impossible to remove without tearing the dura. Scoring was completed without knowledge of treatment at any of the laminectomy sites.

Figure 12:
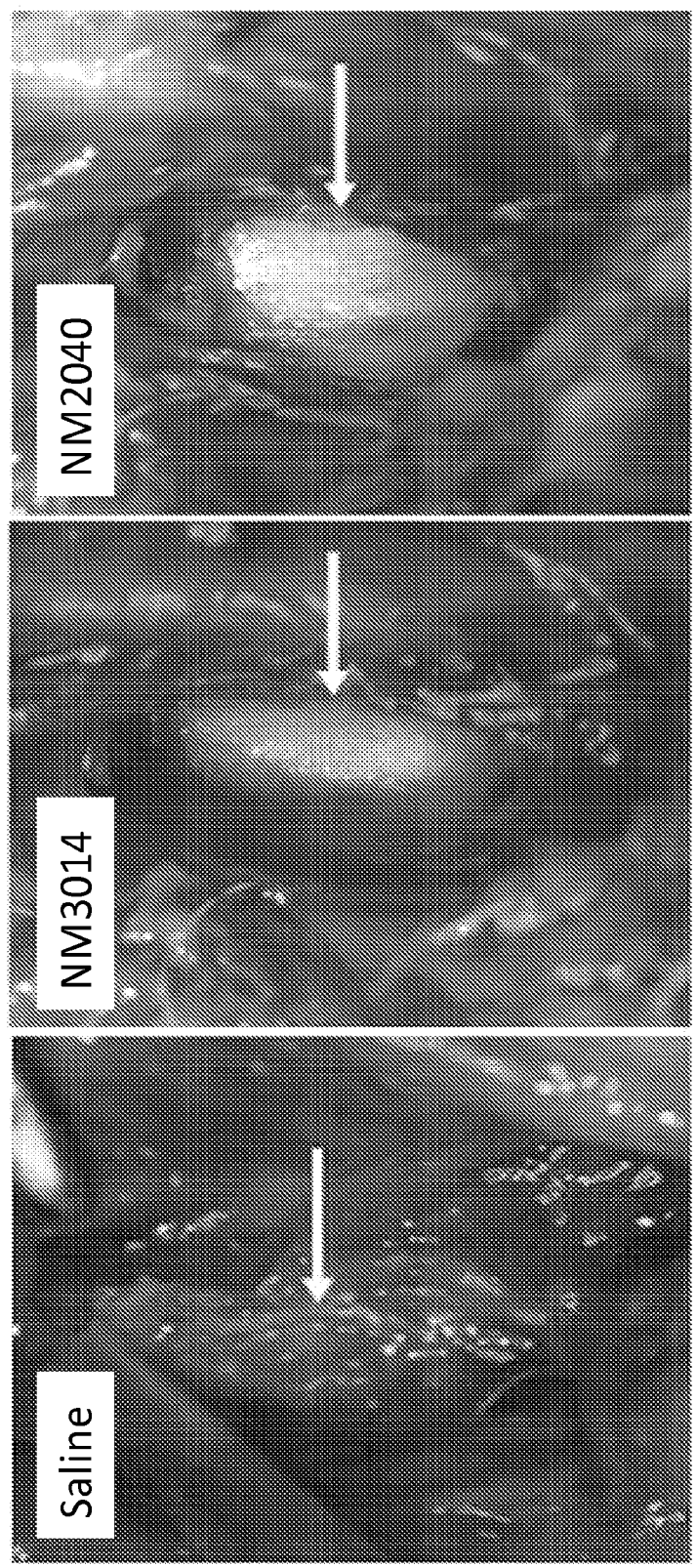
FIG. 12 illustrates laminectomy sites two weeks after placement of A. Saline, B. NM3014, or C. NM2040 showing development of a thick tenacious epidural scar after treatment with saline and thin easily removed connective tissue above the dura after treatment with either NM3014 or NM2040.

FIG. 12 shows that NM2040 is as effective in preventing epidural fibrosis as NM3014. Briefly, for all animals, the skin incision and the underlying fascia and paraspinal muscles had healed well. At all laminectomy sites, separation of the paraspinal muscles revealed a layer of scar tissue. The saline treated site served as a negative control. Sites treated with saline had dense tenacious adhesion. As this scar tissue was removed, bleeding began at the site and dural tears occurred as the scar tissue was removed. As previously observed, sites treated with NM3014, our positive control material had thin easily removed connective tissue above the dura to no adhesions. As for sites treated with NM3014, sites treated with NM2040 also revealed thin easily removed connective tissue above the dura to no adhesions.

Figure 13:
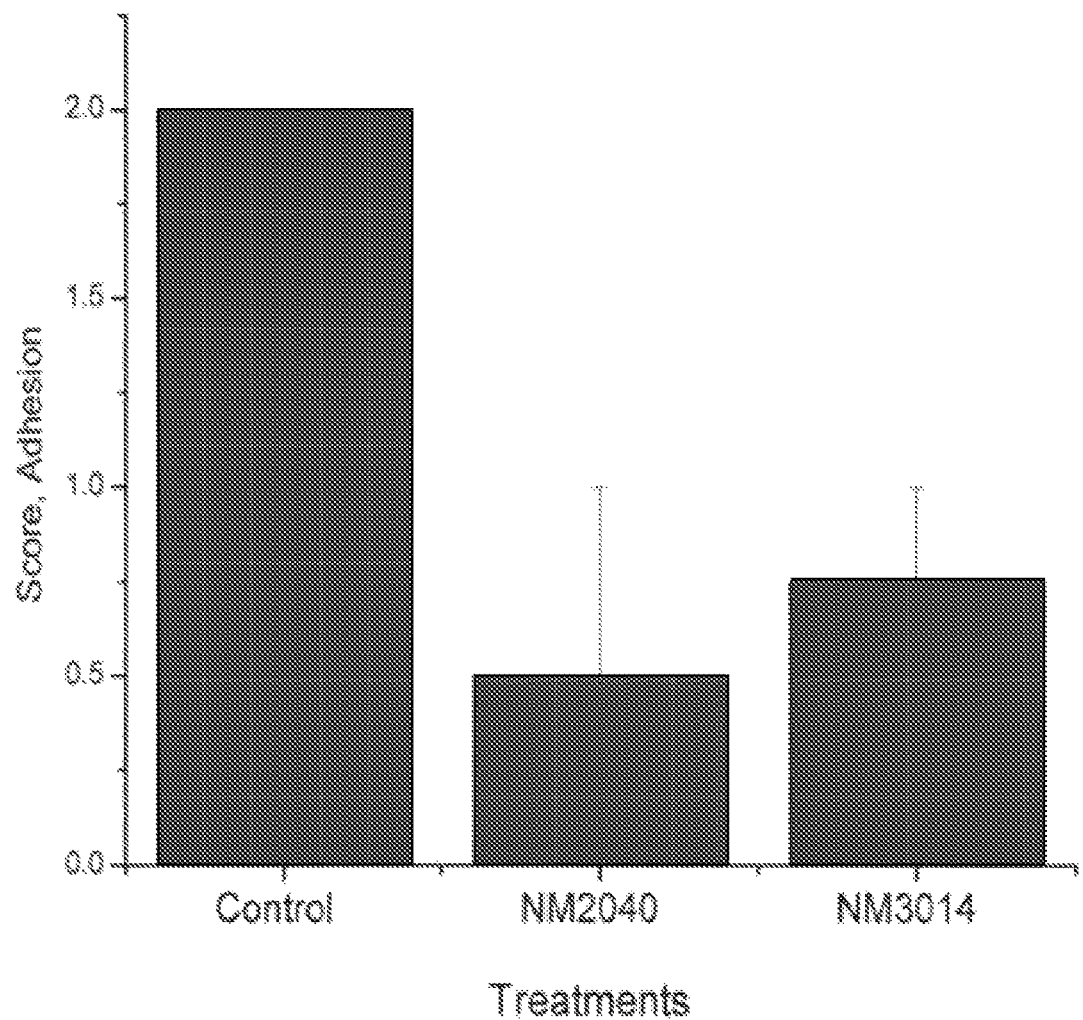
FIG. 13 illustrates treatment with NM2040 was as effective as NM3014 in preventing epidural scar formation after laminectomy. Data represents the Mean scores±SEM of gross evaluation scores for 3 animals in each treatment group. Differences between treatment groups were determined using a Mann-Whitney statistic for non-parametric data. *P<0.05.

FIG. 13 shows the gross evaluations, which confirmed that NM2040 inhibits surgical adhesions in rat laminectomy model. All laminectomy sites that were treated with saline had thick tenacious epidural scars that received scores of 2. In contrast, Laminectomy sites treated with the NM3014 or NM2040 gels received average scores of ~0.75 and 0.5, respectively. Treatment with NM3014 or NM2040 significantly reduces adhesion scores compared to treatment with vehicle. These results demonstrate that NM2040 is a potent agent for reducing epidural fibrosis in the rat laminectomy model. The rat epidural fibrosis model clearly shows that the presence of NM2040 provides a substantial therapeutic benefit by inhibiting fibrosis.

Figure 14:
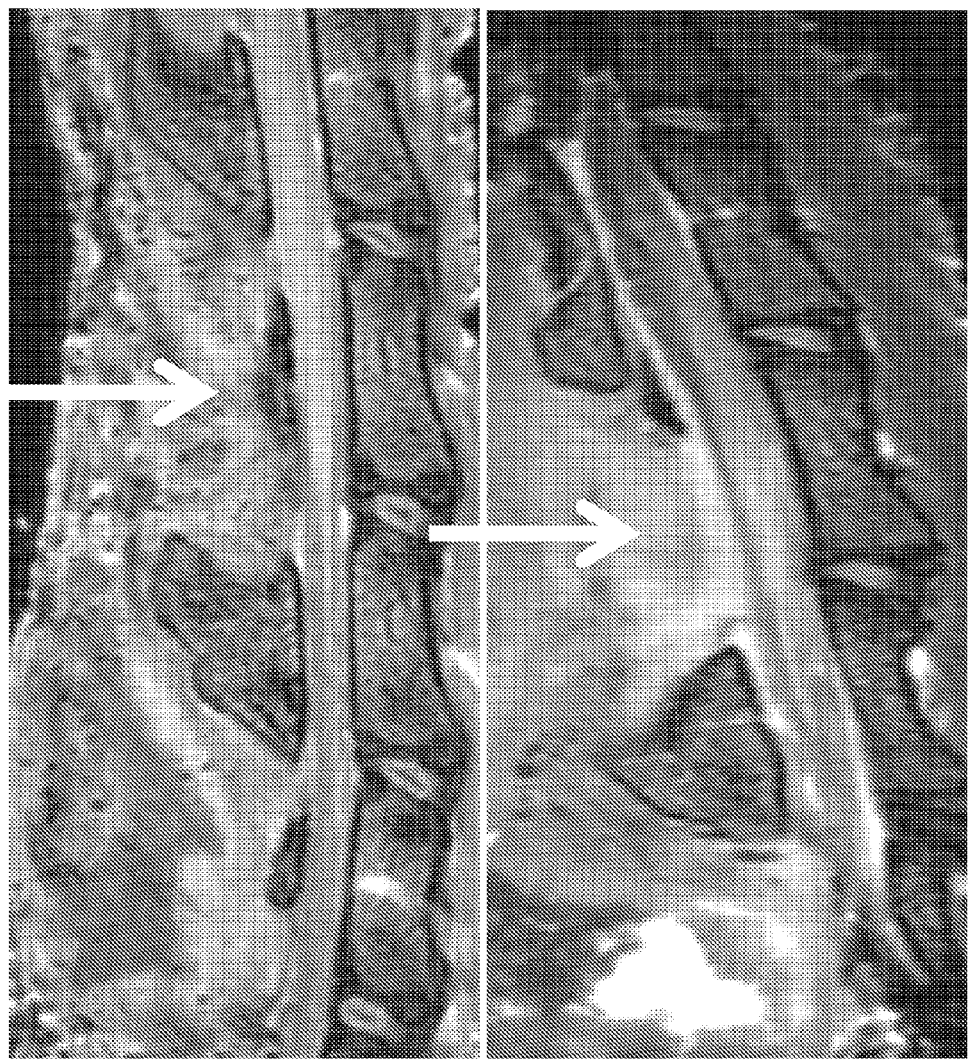
FIG. 14 illustrates laminectomy site shown in sagittal view two weeks after placement of Saline and NM2040. Saline treated animal shows a scar (arrow). NM2040 treated site shows smooth area without tenacious scar.

FIG. 14 shows MRI images of saline and NM2040 treated rats. As shown in the second panel, the area where the arrow is, the tissue appears to be smooth compared to the saline controls.

Figure 15:
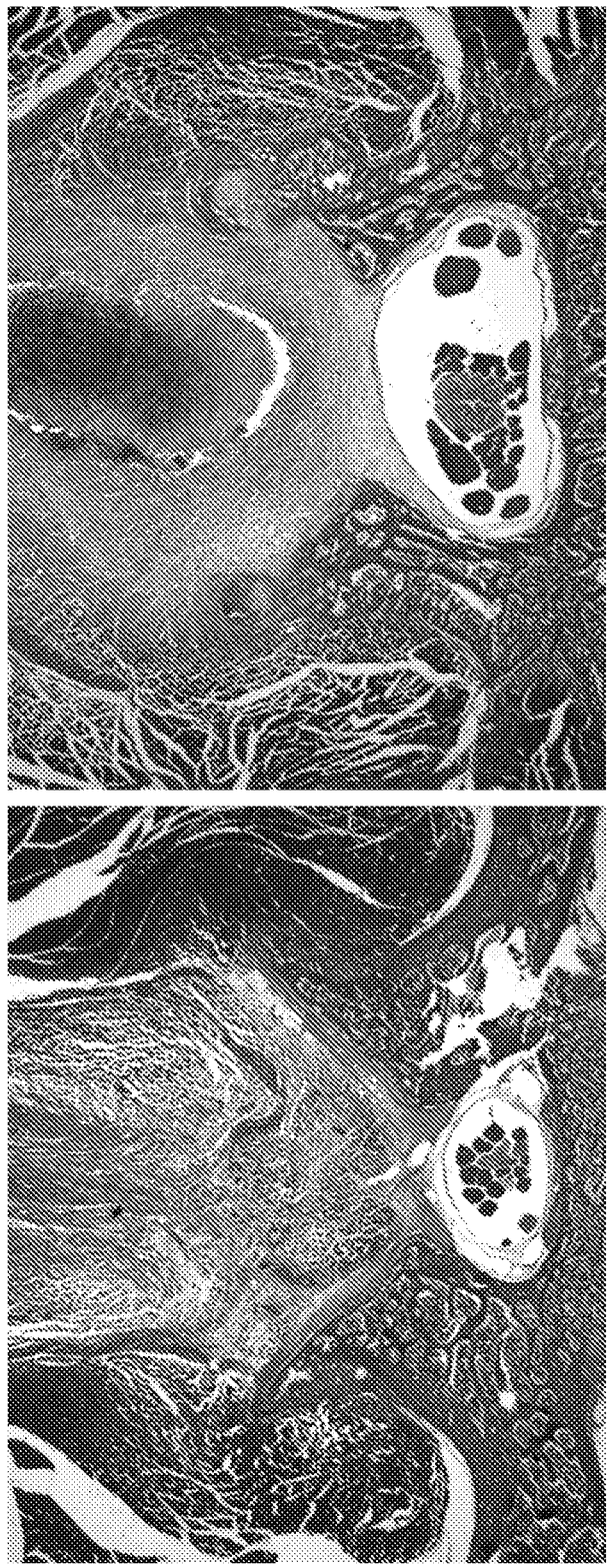
FIG. 15 illustrates laminectomy sites two weeks after placement of Saline and NM2040. Saline treated animals (left two panels from two animals) shows scar near the spinal cord. NM2040 treated site shows smooth area without tenacious scar.

FIG. 15 shows the histological sections of the vertebral column at the L3 level As shown, the NM2040 treated sections have a smooth filling (arrow) compared to the controls which show the presence of bony tissue on the spinal cord. Histology was performed using Masson trichrome staining using standard methods.

Our preliminary data demonstrate that dextran sulfate conjugated to Tirofiban retains the fibroblast anti-proliferative and anti-adhesion properties of dextran sulfate to prevent adhesions after laminectomy. In contrast to NM3014, NM2040 does not destroy platelets.

Having described the invention, the following is claimed:

1. A method for inhibiting cellular proliferation of glioma cells in a mammal comprising:
administering a composition to a mammal wherein the composition includes an amount of a conjugate of dextran sulfate and 2-(butane-1-sulfonylamino)-3-[4-(4-piperidin-4-yl-butoxy)-phenyl]-propionic acid effective to inhibit cellular proliferation of gliomas in the mammal, wherein a secondary amine of 2-(butane-1-sulfonylamino)-3-[4-(4piperidin-4-yl-butoxy)-phenyl]-propionic acid is bonded to the C-1 carbon of the saccharide monomer at the reducing end of dextran sulfate.

2. The method of claim 1, wherein the dextran sulfate has a sulfate content of greater than about 2%.

3. The method of claim 1, wherein the dextran sulfate has an average molecular weight in the range of about 500 Daltons to about 500,000 Daltons.

4. The method of claim 1, wherein the composition is administered after a post surgical procedure that results from a abdominal surgery, joint surgery, tendon surgery, surgery to remove pelvic sidewall adhesions, peritoneal surgery, thoracic surgery, vascular surgery, cardiac surgery, heart bypass surgery, heart valve replacement surgery, or open heart surgery, laminectomy, fallopian tube surgery, plastic surgery, arthritis & osteoarthritis, or surgery to treat temporo-mandibular joint dysfunction.

5. A method for inhibiting neutrophil, monocyte or macrophage invasion in a mammal, comprising:
administering to a surgical site of the mammal where inhibition of neutrophil, monocyte or macrophage invasion is desired an amount of a conjugate of dextran sulfate and 2-(butane-1-sulfonylamino)-3-[4-(4piperidin-4-yl-butoxy)-phenyl]-propionic acid effective to inhibit neutrophil, monocyte or macrophage invasion and effective to prevent platelet activation at the site where inhibition of neutrophil, monocyte or macrophage invasion is desired wherein a secondary amine of 2-(butane-1-sulfonylamino)-3-[4-(4piperidin-4-yl-butoxy)-phenyl]-propionic acid is bonded to the C-1 carbon of the saccharide monomer at the reducing end of dextran sulfate.

6. The method of claim 5, wherein the dextran sulfate has a sulfate content of greater than about 2%.

7. The method of claim 5, wherein the dextran sulfate has an average molecular weight in the range of about 500 Daltons to about 500,000 Daltons.

8. The method of claim 1, wherein the composition is administered after a post surgical procedure that results from a abdominal surgery, joint surgery, tendon surgery, surgery to remove pelvic sidewall adhesions, peritoneal surgery, thoracic surgery, vascular surgery, cardiac surgery, heart bypass surgery, heart valve replacement surgery, or open heart surgery, laminectomy, fallopian tube surgery, plastic surgery, arthritis & osteoarthritis, or surgery to treat temporo-mandibular joint dysfunction.

9. A method for inhibiting glioma cell growth and invasion in a mammal comprising:
   administering to a site of the mammal where inhibition of glioma cell growth is desired an amount of a conjugate of dextran sulfate and 2-(butane-1-sulfonylamino)-3-[4-(4piperidin-4-yl-butoxy)-phenyl]-propionic acid effective to inhibit glioma cell growth, wherein a secondary amine of 2-(butane-1-sulfonylamino)-3-[4-(4piperidin-4-yl-butoxy)-phenyl]-propionic acid is bonded to the C-1 carbon of the saccharide monomer at the reducing end of dextran sulfate.

10. The method of claim 9, wherein said glioma is a metastasis from a primary tumor.

11. The method of claim 9, where inhibition of glioma cell growth around an implant is desired.

\* \* \* \* \*